(12) United States Patent
Cohen, IV et al.

(10) Patent No.: US 12,064,123 B2
(45) Date of Patent: *Aug. 20, 2024

(54) HEMOSTASIS APPARATUS AND METHOD

(71) Applicant: Accumed Radial Systems, LLC, Farmington Hills, MI (US)

(72) Inventors: Mauricio Gabriel Cohen, IV, Miami, FL (US); James Patrick Ryan, Miami, FL (US); James G. Downward, Ann Arbor, MI (US); Joseph R. Korotko, Livonia, MI (US)

(73) Assignee: Accumed Radial Systems, LLC, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/976,695

(22) Filed: Oct. 28, 2022

(65) Prior Publication Data
US 2023/0052744 A1 Feb. 16, 2023

Related U.S. Application Data

(63) Continuation of application No. 13/769,733, filed on Feb. 18, 2013, now Pat. No. 11,701,127.
(Continued)

(51) Int. Cl.
*A61B 17/135* (2006.01)
*A61B 5/00* (2006.01)
(Continued)

(52) U.S. Cl.
CPC .......... *A61B 17/135* (2013.01); *A61B 5/0036* (2018.08); *A61B 5/02438* (2013.01);
(Continued)

(58) Field of Classification Search
CPC .............. A61B 17/132; A61B 17/1322; A61B 17/1327; A61B 17/135; A61B 17/1355;
(Continued)

(56) References Cited

U.S. PATENT DOCUMENTS 2,601,597 A 6/1952 Daniel, Jr. et al.
4,430,566 A 2/1984 Searle
(Continued)

FOREIGN PATENT DOCUMENTS

WO 9846144 10/1998

OTHER PUBLICATIONS

Bengal Radial compression band clinical article review (copyright notice identifies 2011 as the publication date).
(Continued)

*Primary Examiner* — Kankindi Rwego
(74) *Attorney, Agent, or Firm* — Carlson, Gaskey & Olds, P.C.

(57) ABSTRACT

The apparatus and method for hemostasis that informs the provider as to whether the appropriate magnitude of pressure is being applied to a puncture site on a patient. A visual pulse indicator can visually convey whether or not there is proper blood flow at the puncture site based on the pulsing motion encountered by the visual pulse indicator on the puncture site. The visual pulse indicator can potentially factor in a variety of different input parameters in displaying information that is useful to providers.

15 Claims, 10 Drawing Sheets

Related U.S. Application Data

(60) Provisional application No. 61/695,291, filed on Aug. 30, 2012, provisional application No. 61/634,772, filed on Mar. 6, 2012.

(51) Int. Cl.
*A61B 5/024* (2006.01)
*A61B 5/026* (2006.01)
*A61B 17/132* (2006.01)
*A61B 17/00* (2006.01)

(52) U.S. Cl.
CPC .............. *A61B 5/026* (2013.01); *A61B 5/445* (2013.01); *A61B 5/742* (2013.01); *A61B 17/1325* (2013.01); *A61B 5/6831* (2013.01); *A61B 2017/00119* (2013.01); *A61B 2017/00123* (2013.01); *A61B 2017/00132* (2013.01); *A61B 2017/00199* (2013.01); *A61B 17/1355* (2013.01)

(58) Field of Classification Search
CPC ... A61B 5/02438; A61B 5/026; A61B 5/6831; A61B 5/02; A61B 5/02042; A61B 5/02233; A61B 5/0261; A61B 5/11; A61B 5/1114

See application file for complete search history.

(56) References Cited

U.S. PATENT DOCUMENTS

| | | | |
|---|---|---|---|
| 4,509,528 A | 4/1985 | Sahota | |
| 5,000,745 A | 3/1991 | Guest et al. | |
| 5,269,803 A | 12/1993 | Geary et al. | |
| 5,279,303 A | 1/1994 | Kawamura et al. | |
| 5,376,067 A | 12/1994 | Daneshvar | |
| 5,643,315 A | 7/1997 | Daneshvar | |
| 5,792,173 A | 8/1998 | Breen et al. | |
| 5,935,077 A | 8/1999 | Ogle | |
| 6,264,673 B1 | 7/2001 | Egneloev et al. | |
| 6,331,186 B1 | 12/2001 | Wang et al. | |
| 6,414,761 B1 | 7/2002 | Stepanek | |
| 6,475,153 B1 | 11/2002 | Khair et al. | |
| 6,572,636 B1 | 6/2003 | Hagen et al. | |
| 6,575,933 B1 | 6/2003 | Wittenberger et al. | |
| 6,634,364 B2 | 10/2003 | Westlund et al. | |
| 6,647,986 B1 | 11/2003 | Korotko et al. | |
| 6,846,321 B2 | 1/2005 | Zucker | |
| 7,479,149 B2 | 1/2009 | Pallazza | |
| 7,498,477 B2 | 3/2009 | Wada et al. | |
| 7,622,628 B2 | 11/2009 | Bergin et al. | |
| 7,824,340 B2 | 11/2010 | Lee et al. | |
| 7,927,295 B2 | 4/2011 | Bates et al. | |
| 8,180,427 B2 | 5/2012 | Phua et al. | |
| 11,701,127 B2 * | 7/2023 | Cohen | A61B 5/445 600/502 |
| 2001/0027337 A1 | 10/2001 | Di Caprio | |
| 2002/0169404 A1 | 11/2002 | Olderr | |
| 2004/0098035 A1 | 5/2004 | Wada et al. | |
| 2004/0109964 A1 | 6/2004 | Beckham | |
| 2004/0122469 A1 | 6/2004 | Akerfeldt et al. | |
| 2004/0147956 A1 | 7/2004 | Hovanes et al. | |
| 2004/0229004 A1 | 11/2004 | Spice et al. | |
| 2004/0243044 A1 | 12/2004 | Penegor et al. | |
| 2004/0249342 A1 | 12/2004 | Khosravi et al. | |
| 2005/0010297 A1 | 1/2005 | Watson et al. | |
| 2006/0079727 A1 | 4/2006 | Chernomorsky et al. | |
| 2006/0182913 A1 | 8/2006 | Barry et al. | |
| 2007/0010788 A1 | 1/2007 | Evans | |
| 2007/0118162 A1 | 5/2007 | Abi-Kheirs | |
| 2007/0287923 A1 | 12/2007 | Adkins et al. | |
| 2008/0071202 A1 | 3/2008 | Nardi et al. | |
| 2008/0076982 A1 | 3/2008 | Ollerdessen et al. | |
| 2008/0097512 A1 | 4/2008 | Sidwell et al. | |
| 2008/0269659 A1 | 10/2008 | Bergin et al. | |
| 2009/0081917 A1 | 3/2009 | Greenwald | |
| 2009/0138039 A1 | 5/2009 | Wada et al. | |
| 2009/0281565 A1 | 11/2009 | McNeese | |
| 2010/0160908 A1 | 6/2010 | Sampson et al. | |
| 2010/0249906 A1 | 9/2010 | Zamore | |
| 2010/0280541 A1 | 11/2010 | Lampropoulos et al. | |
| 2010/0286726 A1 | 11/2010 | Chalfoun et al. | |
| 2011/0178415 A1 | 7/2011 | Baldwin et al. | |
| 2013/0085524 A1 | 4/2013 | Dahlberg et al. | |

OTHER PUBLICATIONS

Merit Medical Band brochure (publication date unknown).
QuickClot Hemostasis Bandage brochure (publication date unknown).
Terumo TR Band brochure (publication date unknown).
Vascular Solutions D-Stat Rad-Band brochure (copyright notice identifies 2010 as the publication date).

* cited by examiner

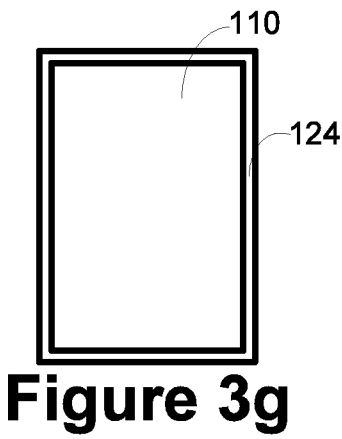
Figure 3g
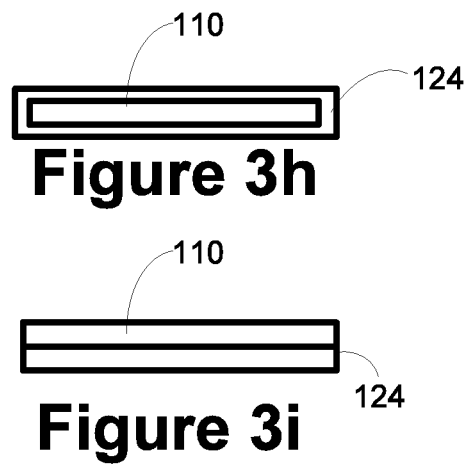
Figure 3h
Figure 3i
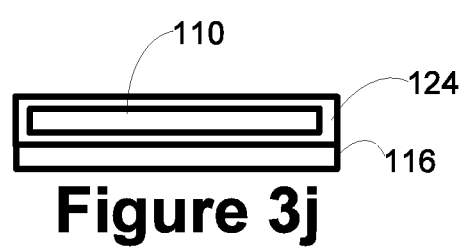
Figure 3j
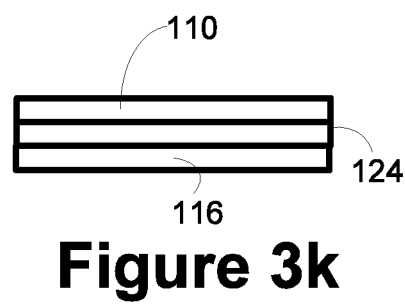
Figure 3k
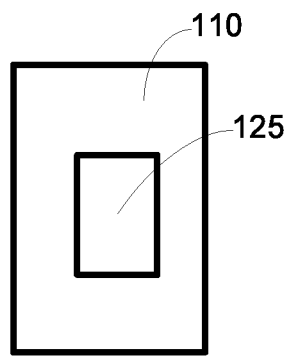
Figure 3l
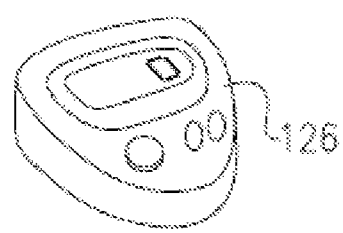
Figure 4a
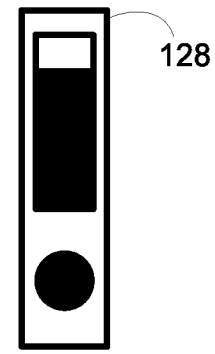
Figure 4b

HEMOSTASIS APPARATUS AND METHOD

RELATED APPLICATIONS

This utility patent application is a continuation of U.S. patent application Ser. No. 13/769,733 filed Feb. 18, 2013; which claims priority to U.S. Provisional Patent Application No. 61/634,772 filed Mar. 6, 2012 and U.S. Provisional Patent Application No. 61/695,291 filed Aug. 30, 2012; the disclosures of which are incorporated by reference in their entirety herein.

BACKGROUND OF THE INVENTION

The invention is a hemostasis apparatus and method (collectively the "apparatus"). More specifically, the invention is an apparatus that uses a visual pulse indicator to identify a suitable magnitude of pressure for use in stopping the bleeding of a patient.

Hemostasis means "the stoppage of bleeding". There are many contexts in the providing of healthcare to patients when it is necessary to address the bleeding or hemorrhage of a patient. Bleeding can result from a variety of unintentional causes (collectively the "medical condition" of the patient) as well as variety of intentional causes (collectively the "medical treatment" of the patient).

Examples of medical conditions that can trigger a need for hemostasis can include but are not limited to: diseases; disorders; injuries; allergies; and other conditions that relate to the patient (collectively "medical conditions"). Medical conditions will often trigger the need for medical treatments.

Examples of medical treatments that can trigger a need for hemostasis can include but are not limited to: catheterizations; blood tests; the direct injection of medicine into the body; and other treatments and diagnostic activities that involve puncturing the skin of a patient (collectively "medical treatments"). One common category of treatments that typically results in bleeding is intravascular catheterization. Cardiac catheterizations are a subset of intravascular catheterizations and are commonly used to diagnose and treat heart conditions.

Whether the need for hemostasis is triggered by a condition of the patient or the treatment of the patient, hemostasis typically involves the application of pressure or force over the location of the wound (the "puncture site") on the patient. In the context of catheterizations, the term "arteriotomy" is synonymous with puncture site. If too little pressure is used, the bleeding will not be stopped and the patient is harmed by blood loss. If too much pressure is used, blood flow in the patient will be constricted and the patient is harmed by the constricted blood flow.

Conventional hemostasis tools do not provide a convenient way to monitor the pressure applied to the puncture site. The failure of conventional tools to provide such information results in a missed opportunity to selectively adjust the pressure applied to the puncture site.

SUMMARY OF THE INVENTION

The invention is a hemostasis apparatus and method (collectively the "apparatus"). More specifically, the invention is an apparatus that uses a visual pulse indicator to identify a suitable magnitude of pressure for use in stopping the bleeding of a patient.

Hemostasis means "the stoppage of bleeding". Use of the apparatus allows the person performing hemostasis to selectively adjust the pressure applied to the location of the wound (the "puncture site") on the patient in response to information conveyed by the visual pulse indicator.

The apparatus can be implemented in a wide variety of different configurations using a wide variety of different components. In some embodiments, the apparatus can be implemented in a fully integrated manner with the device that actually applies the pressure to the wound or puncture site. In other embodiments, the apparatus can be entirely separate from the device that is actually stopping the bleeding of the patient. In still other embodiments, the apparatus may be implemented in a variety of partially integrated configurations between the two extremes of complete integration and complete separation.

BRIEF DESCRIPTION OF THE DRAWINGS

Many features and inventive aspects of the apparatus are illustrated in the following drawings:

FIG. 3g is a diagram illustrating an example of a front-view of a visual pulse indicator enveloped within a sheath.

FIG. 3h is a diagram illustrating an example of a side-view of a visual pulse indicator enveloped within a sheath.

FIG. 3i is a diagram illustrating an example of a side-view of a visual pulse indicator with a sheath underneath the visual pulse indicator.

FIG. 3j is a diagram illustrating an example of the apparatus illustrated in FIG. 3h that includes an anti-adhesion component, such as a medical grade silicone coating.

FIG. 3k is a diagram illustrating an example of the apparatus illustrated in FIG. 3i that includes an anti-adhesion component, such as a medical grade silicone coating.

FIG. 3l is a diagram illustrating an example of the apparatus with a window in the center of the visual pulse indicator to facilitate direct viewing of the puncture site.

FIG. 4a is a diagram illustrating an example of a timing component that can display elapsed time using a variety of different numerical metrics.

FIG. 4b is a diagram illustrating an example of a timing component that is based on the release of ink within a strip.

DETAILED DESCRIPTION

The invention is a hemostasis apparatus and method (collectively the "apparatus"). More specifically, the invention is an apparatus that uses a visual pulse indicator to identify a suitable magnitude of pressure for use in stopping the bleeding of a patient. Hemostasis means "the stoppage of bleeding".

I. Alternative Embodiments

No patent application can expressly disclose in words or in drawings, all of the potential embodiments of an invention. In accordance with the provisions of the patent statutes, the principles and modes of operation of the apparatus are explained and illustrated in certain preferred embodiments. However, it must be understood that the apparatus may be practiced otherwise than is specifically explained and illustrated without departing from its spirit or scope.

The description of the apparatus provided below should be understood to include all novel and non-obvious combination of elements described herein, and claims may be presented in this or a later application to any novel non-obvious combination of these elements. Moreover, the foregoing embodiments are illustrative, and no single feature or element is essential to all possible combinations that may be claimed in this or a later application.

II. Overview

Figure 1A:
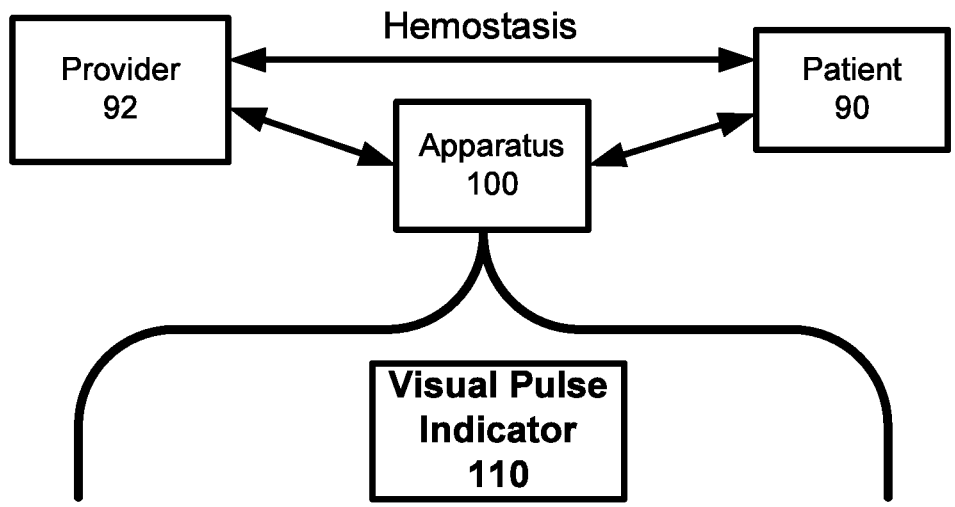
FIG. 1a is a block diagram illustrating an example of an interaction between a patient and healthcare provider that involves use of the apparatus to perform hemostasis.

FIG. 1a is a block diagram illustrating an example of an interaction between a patient 90 and healthcare provider 92 that involves use of an apparatus 100 to perform hemostasis. Many if not most hemostasis processes involve the application of pressure to the location of a cut or wound (the "puncture site") on the patient. If insufficient pressure is used over the puncture site, the bleeding will not be stopped and the patient 90 is harmed by blood loss. If too much pressure is used, blood flow in the patient 90 that is downstream from the puncture site will be constricted and the patient 90 is harmed by the constricted blood flow.

Figure 2:
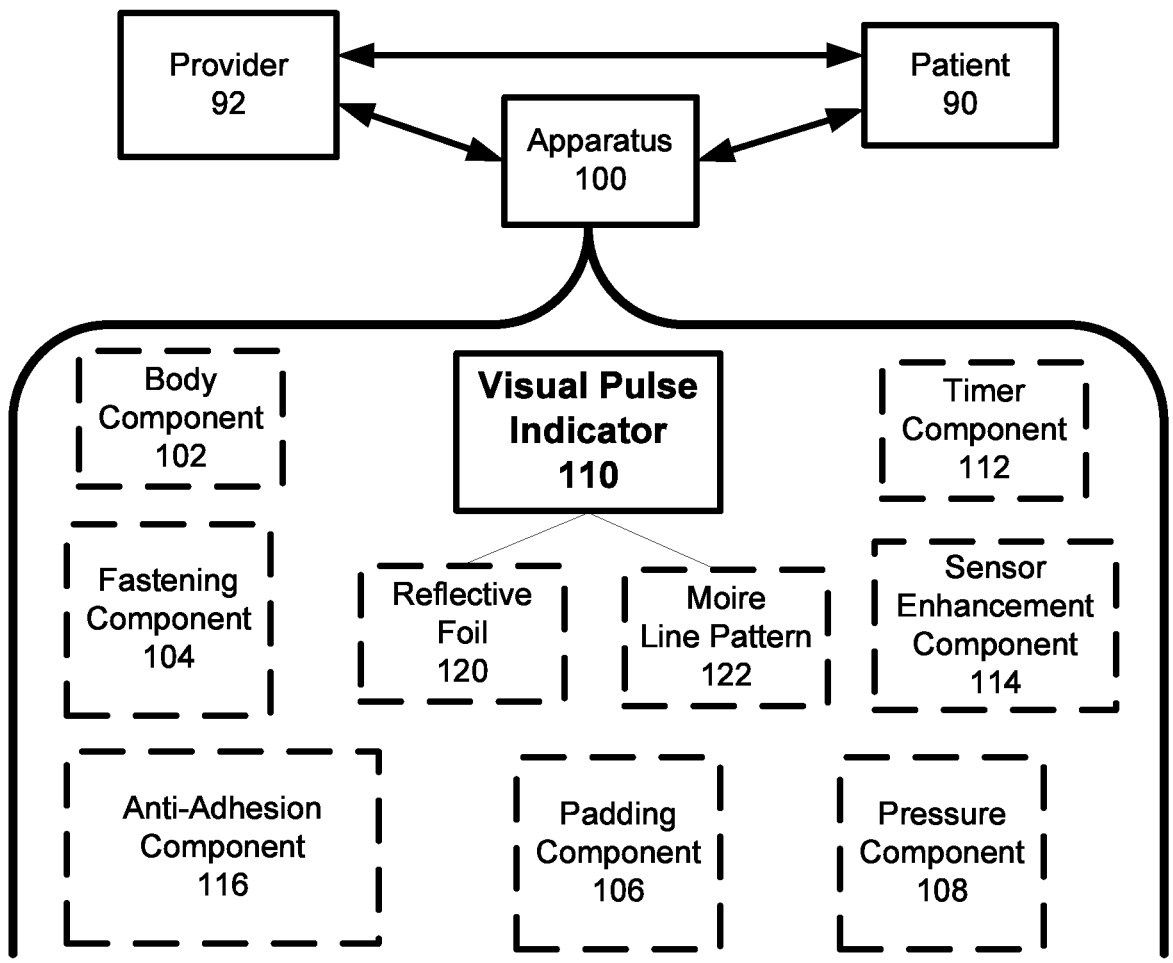
FIG. 2 is a block diagram illustrating examples of different components that can be incorporated into the apparatus.

The apparatus 100 uses the visual pulse indicator 110 to determine whether or not the appropriate magnitude of pressure is being applied to the puncture site. By providing the functionality of a visual pulse indicator 110, feedback can be provided to the provider 92 of hemostasis as to whether the magnitude of pressure applied to the puncture site should be adjusted. As discussed below and as illustrated in FIG. 2, a wide variety of different components can be used in conjunction with the visual pulse indicator 110 in the hemostasis process. The apparatus 100 with the visual pulse indicator 110 can be a non-integrated stand-alone device as illustrated in FIG. 1a that works in conjunction with other non-attached hemostasis components. On the other end of the continuum, the apparatus 100 can be embodied in a fully integrated apparatus 100 that includes all of the components required or desired for hemostasis. The apparatus 100 can also be implemented in a partially integrated manner in a wide variety of different ways that exist between the extreme poles of pure stand-alone embodiments and 100% integrated embodiments.

Figure 1B:
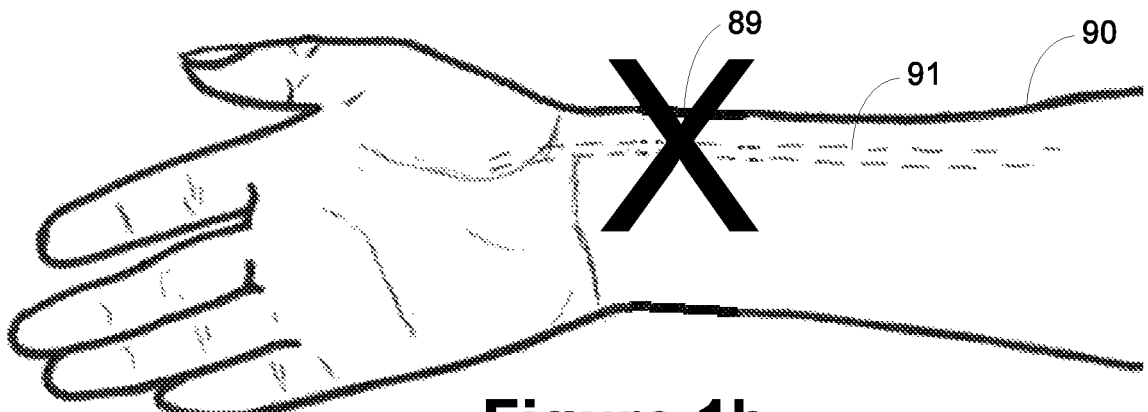
FIG. 1b is an environmental diagram illustrating an example of a puncture site on a patient as part of a transradial cardiac catheterization treatment.

FIG. 1b is an environmental diagram illustrating an example of a puncture site 89 on a patient 90 as part of a transradial cardiac catheterization treatment. As illustrated in the figure, the puncture site 89 is on a radial artery 91 on the wrist of the patient 90. Different examples of medical conditions and medical treatments will involve different puncture sites 89, different apparatus 100 dimensions, and different component configurations. Transradial cardiac catheterization was the original inspiration behind the conception of the apparatus 100, but the concepts, components, and methods of operations are clearly applicable to other contexts. Although pressure is applied to the puncture site 89, the visual pulse indicator 110 need not be positioned on the puncture site 89. It is possible for the visual pulse indicator 110 to be positioned downstream from the puncture site 89. Different medical treatments can impact the locations at which the visual pulse indicator 110 can be used. For example, in the context of transradial cardiac catheterization, the branching out of a single artery into two arteries and the subsequent downstream convergence of those two arteries at the wrist means that a visual pulse indicator 110 could potentially be positioned anywhere between the puncture site 89 and the wrist.

Figure 1C:
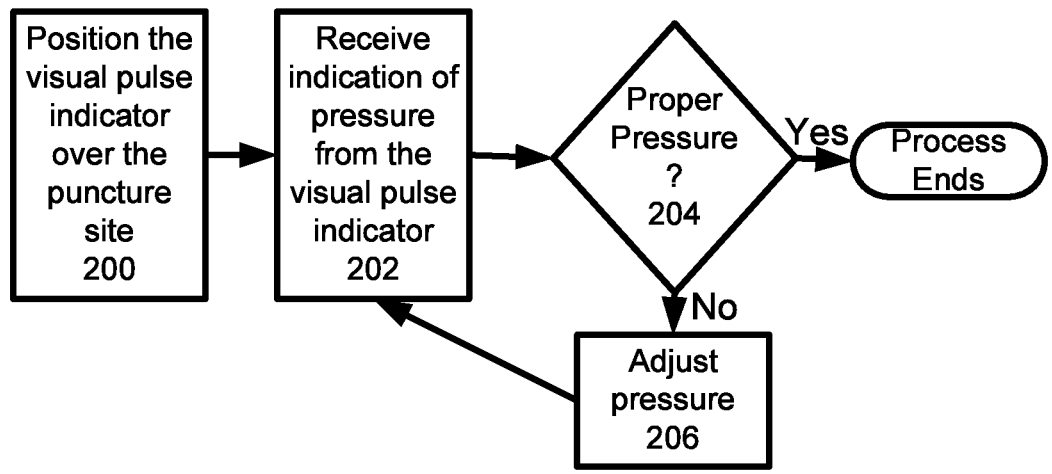
FIG. 1c is a flow chart diagram illustrating an example of a method for performing hemostasis using a visual pulse indicator.

FIG. 1c is a flow chart diagram illustrating an example of a method for performing hemostasis using a visual pulse indicator 110. At 200, the visual pulse indicator 110 is positioned over the puncture site 89. Different ways of securing the position of the visual pulse indicator 110 with respect to the puncture site 89 are discussed below. At 202, information from the visual pulse indicator is conveyed to the provider 92. As discussed below, there are a wide variety of different ways in which the visual pulse indicator 110 can make the applicable information accessible to the provider 92. At 204, the provider 92 can determine whether or not the currently applied magnitude of pressure over the puncture site 89 is appropriate or whether it should be adjusted based on the information provided by the visual pulse indicator 110.

If no adjustment is desirable at 204 the process can then end. If an adjustment is desired at 204, then the adjustment can be made at 206. The process can then loop back to 202, where a fresh reading of the visual pulse indicator 110 is conveyed at 202. The loop between 202 through 206 can repeat until the magnitude of pressure applied to the puncture site 89 is appropriate.

The process shown in FIG. 1c can be applicable during the entire hemostasis treatment of the patient 90. The process can also be applicable when the apparatus 100 is first applied to the patient 90, or anytime during recovery of the patient 90.

Adequate blood flow at the puncture site 89 without bleeding and downstream from the puncture site 89 is an important requirement of successful hemostasis.

Figure 1D:
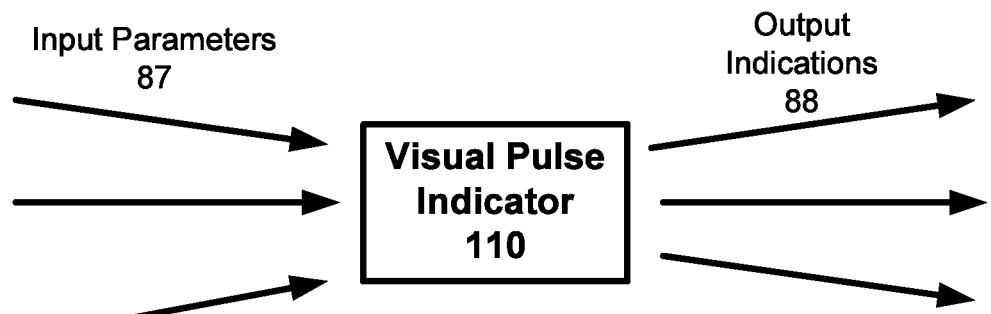
FIG. 1d is an input-output diagram illustrating an example of multiple inputs to and multiple outputs from the visual pulse indicator.

FIG. 1d is an input/output diagram pertaining to a visual pulse indicator 110. Different embodiments of the apparatus 100 can provide for being responsive to different types of input parameters 87 (such as frequency of pulse, magnitude of force pulse, and distance from puncture site 89) and different numerical values associated with the particular input type (a numerical value indicating a measure of frequency, magnitude of pulse, or a distance from the puncture site 89).

Similarly, different embodiments of the apparatus 100 can also provide for displaying a variety of different output indications 88 (which can also be referred to as indicia, indicators, displays, or outputs). The visual pulse indicator 110 can also involve different types and magnitudes of output indications 88.

In the context of a visual pulse indicator 110 comprised of a thin flexible film, examples of potential input parameters 87 can include the magnitude of a pulse motion, the frequency of a pulse, a period of time between pulses, a distance from a puncture site 89, and potentially other variables. In the context of a visual pulse indicator 110 comprised of a thin flexible film, examples of potential display indications 88 can include changes of color, surface area on the film, frequency of changes in the display, duration of time between changes in what is displayed, and potentially other indicia.

Output displays 88 from the visual pulse indicator 110 can differentiate between different inputs types as well as between different inputs of the same type. For example, the apparatus 100 can be used to differentiate between satisfactory pressure at the puncture site 89 and a state of too much pressure being applied to the puncture site 89. This differentiation is communicated to providers 92 through one or more display indicators 88, such as the frequency of color changes on a thin film serving as the visual pulse indicator 110.

III. Definitions and Introduction of Elements

FIG. 2 is a block diagram illustrating an example of interaction between a patient 90 and healthcare provider 92 using the apparatus 100, and different components that can be incorporated into the apparatus 100.

The apparatus 100 is a device used in the treatment of patients 90.

A. Patient

A patient 90 is typically a human being, although the apparatus 100 (or alternative variations thereof) can also be used in the treatment of potentially any organism capable of bleeding. Thus, a variety of different embodiments of the apparatus 100 can be used at zoos, farms, veterinary clinics, and other settings where non-human animals are give medical treatment.

In the context of human beings, patients 90 can vary widely in terms of age, size, gender, weight, medical status, and other attributes. The original inspiration leading to the conception of the apparatus 100 was for the apparatus 100 to be used in the context of cardiac catheterization. It is anticipated that the apparatus 100 may be particularly useful in the context of transradial catheterizations. However, the apparatus 100 (or alternative variations thereof) can also be used in a variety of contexts that involve vascular care and the treatment of wholly different conditions.

In some instances and embodiments of the apparatus 100, the patient 90 can apply and utilize the apparatus 100 without the assistance of any other person, much less the assistance of a healthcare provider 92 such as a physician, physician's assistant, nurse, paramedic, or other form of caregiver. However, in most instances, the apparatus 100 will be used in the context of a potentially broad range of interactions between the patient 90 and the provider 92. In many embodiments, it will be desirable to place the apparatus 100 directly on top of the puncture site 89. However, the visual pulse indicator 110 can also be used downstream from the puncture site 89. In the case of transradial cardiac catheterization, the maximum distance between the puncture site 89 and the location of a further downstream application of the visual pulse indicator 110 is limited by human anatomy because branching arteries re-combine in the palm of the hand of the patient 90. This means that there is a relatively narrow area along the artery 91 in which one of the arteries can be effectively isolated from the other. In some ways, it is the relatively narrow space for such measurements that causes the prior art to teach away from the apparatus 100.

B. Provider

A provider 92 is typically a healthcare professional such as a physician, physician's assistant, nurse, paramedic, or other form of caregiver. In some contexts, the provider 92 could be a family member, friend, or other type of non-professional provider of services or even the patient 90 engaging in self-treatment.

The range of potential providers 92 who may find the apparatus 100 desirable is commensurate with the broad range of contexts that the apparatus 100 can be used. For example, in the context of treating animals, the provider 92 could be a veterinarian or veterinarian's assistant. In the context of human patients 90, the apparatus 100 can be used in the context of a variety of different treatment protocols and a variety of different medical conditions.

The wide range of potentially different providers 92 is commensurate with the wide variety of potentially different puncture sites 89 and patients 90.

C. Apparatus

The apparatus 100 uses the visual pulse indicator 110 to provide feedback to a provider 92 as to whether the appropriate magnitude of pressure is being applied to the puncture site 89. The apparatus 100 may or may not be the device that actually supplies pressure to the puncture site of the patient 90.

The apparatus 100 can be used in a variety of different contexts, but it is often used as part of a large set of interactions between the patient 90 and the provider 92. Hemostasis is often performed in a broader context of medical treatment.

As discussed both above and below, the apparatus 100 can be implemented in a variety of different component configurations. On one end of the continuum is a stand-alone apparatus 100 that is comprised solely of a visual pulse indicator 110 and no other components. In a fully stand-alone implementation, the functions such as the application of pressure on the puncture site 89 are provided by a separate device. On the other end of the continuum is a fully integrated apparatus 100 that includes all of the components illustrated in FIG. 2. Between these two polar opposites are a large number of different component configurations. The reason why all of the component boxes except the visual pulse indicator 110 are illustrated with dotted lines is because such components are optional.

1. Visual Pulse Indicator

The visual pulse indicator 110 is a component of the apparatus 100 that provides information regarding a blood flow attribute of the patient 90. The visual pulse indicator 110 is positioned on the puncture site 89. Different embodiments of the visual pulse indicator 110 can assess/measure different blood flow attributes and then communicate the information to the provider 92 in a variety of different ways. Different embodiments of the visual pulse indicator 110 can distinguish between proper pressure/unconstricted blood flow and excessive pressure/constricted blood flow. The visual pulse indicator 110 can also be used to identify instances of insufficient pressure.

One effective approach can be to utilize the physical pulsing motion of the artery 91 and the flowing blood under the puncture site 89. The pulsing motion of the artery 91 at the puncture site 89 can differentiate between a properly pressured puncture site 89 (where blood is flowing unconstructed) versus a situation where blood flow is constricted due to excessive pressure. The frequency, duration, and/or magnitude of the pulses and other input factors/parameters 87 impact the visual pulse indicator 110 because the visual pulse indicator 110 is a thin film onto which the pulse or other input parameters 87 are propagated onto.

Just as different visual pulse indicators 110 can be triggered by different inputs or triggers, visual pulse indicators 110 can also convey a wide variety of different outputs (which can also be referred to as indicia or indications). Colors, specific designs, pulsing light, and other indicia or outputs 88 can be generated by different types of visual pulse indicators 110.

Figure 3A:
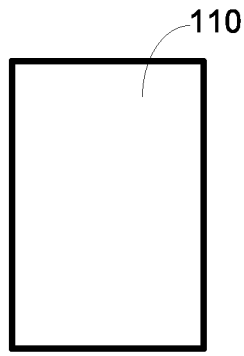
FIG. 3a is a diagram illustrating an example of a top-view of visual pulse indicator comprised of a thin film.
Figure 3B:
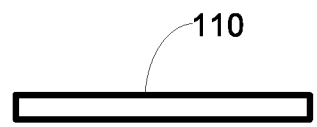
FIG. 3b is a diagram illustrating an example of a side-view of a visual pulse indicator comprised of a thin film.

FIG. 3a is a diagram illustrating an example of a top-view of visual pulse indicator 110 comprised of a thin film. FIG. 3b is a diagram illustrating an example of a side-view of a visual pulse indicator comprised of a thin film. The film will typically be less than a millimeter in thickness because thin film will better respond to the physical stimulus of the pulsing artery and blood flow (including arterial movement). A stand-alone embodiment of the apparatus 100 can be comprised solely of the thin film illustrated in FIGS. 3a and 3b that is placed on the puncture site 89 and held in position by a separate source of pressure, such as a conventional hemostasis band. In other embodiments, the visual pulse indicator 110 is one component in an integrated delivery system for providing hemostasis to a patient 90. Many partially-integrated variations can exist between those two polar opposites.

a. Reflective Foil/Surface

Figure 3C:
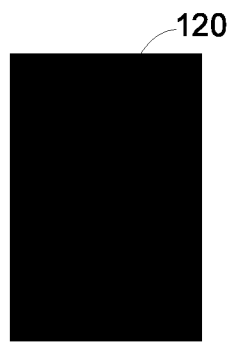
FIG. 3c is a diagram illustrating an example of a top-view of a visual pulse indicator comprised of a reflective foil.
Figure 3D:
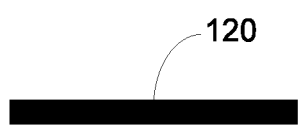
FIG. 3d is a diagram illustrating an example of a side-view of a visual pulse indicator comprised of a reflective foil.

FIG. 3c is a diagram illustrating an example of a top-view of a visual pulse indicator 110 comprised of a reflective foil 120, which can also be referred to as a reflective surface 120. FIG. 3d is a diagram illustrating an example of a side-view of a visual pulse indicator 110 comprised of a reflective foil 120. There are a wide variety of different reflective materials that can be used to comprise the reflective foil 120, including but not limited to polyester. The foil 120 moves with pulsing blood up and down, changing color with each cycle (typically from red to yellow, although different color configurations are possible). When too much pressure is applied to the puncture site 89, blood flow is constricted and visual pulsation is not seen. When too little pressure is applied to the puncture site, a relatively small portion of the reflective foil 120 displays any type of color and bleeding may occur.

b. Moire Patterns

Figure 3E:
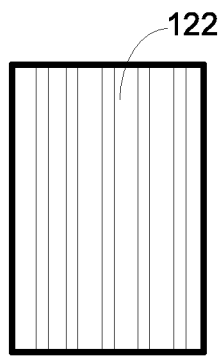
FIG. 3e is a diagram illustrating an example of a top-view of a visual pulse indicator comprised of a Moire pattern.
Figure 3F:
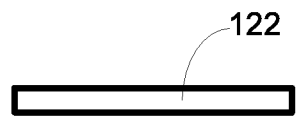
FIG. 3f is a diagram illustrating an example of a side-view of a visual pulse indicator comprised of a Moire pattern.

Moire line patterns are known in the prior art, and such patterns can be used by visual pulse indicators 110. FIG. 3e is a diagram illustrating an example of a top-view of a visual pulse indicator 110 comprised of a Moire pattern 122. FIG. 3f is a diagram illustrating an example of a side-view of a visual pulse indicator 110 comprised of a Moire pattern 122.

Moire patterns are two images capable of moving with respect to each other, forming in the aggregate a different image than the two composite images. For example, two lines could combine to form a single line in response to the vibrations generated by the pulse at the puncture site 89. A wide variety of different patterns could be used in conjunction with the visual pulse indicator 110.

c. Sheath

Visual pulse indicators 110 can also include a variety of different components to either enhance the effectiveness of the visual pulse indicator 110, or to protect the structure and preserve the functionality of the visual pulse indicator 110.

FIG. 3g is a diagram illustrating an example of a front-view of a visual pulse indicator 110 enveloped within a sheath 124. A sheath is typically comprised of a transparent or at least substantially transparent plastic, such as polyurethane or polyvinyl chloride (PVC). In many embodiments, the visual pulse indicator 110 is connected to the balloon 140 or some other pressure component 108, in which case the sheath 124 is a compartment, surface, or set of surfaces that keeps other components and environmental factors (such as blood) from coming into contact with the thin flexible film of the visual pulse indicator 110.

FIG. 3h is a diagram illustrating an example of a side-view of a visual pulse indicator enveloped within a sheath 124. FIG. 3i is a diagram illustrating an example of a side-view of a visual pulse indicator 110 with a sheath 124 underneath the visual pulse indicator 110, but without enveloping the visual pulse indicator 110.

Figure 7A:
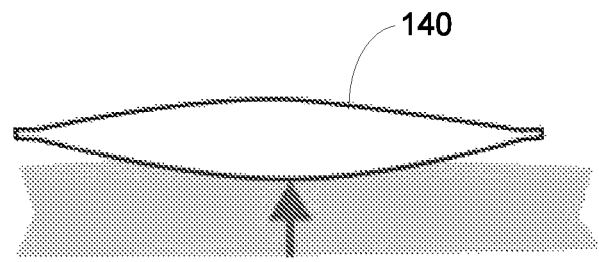
FIG. 7a is a diagram illustrating an example of a side view of pressure component in the form of a balloon.
Figure 7B:
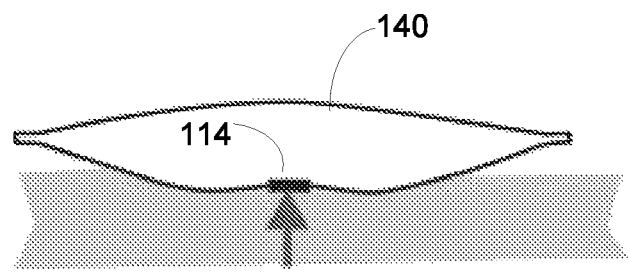
FIG. 7b is a diagram illustrating an example of a side view of pressure component in the form of a balloon with a strip in the center of a bottom surface of the balloon.

The series of FIGS. 3a through 3k show the visual pulse indicator 110 in the geometric shape of a rectangle. It is anticipated that other alternative geometric shapes may be applicable or otherwise desirable. The visual pulse indicator 110 may also include a feature to allow the provider 92 to better view the puncture site 89. The visual pulse indicator may be "see through" in design or construction while still being able to provide feedback 202, 204 and 206 to the provider 92. One embodiment is a visual pulse indicator 110 with an included "window" 125 as illustrated in FIGS. 31 and 7d. The visual pulse indicator 110 is placed over the puncture site 89 with the puncture site 89 inside the window 125. This allows the provider 92 to see the puncture site 89. The remainder of the visual pulse indicator 110 is all around the area proximate to the puncture site 89 and provides feedback 202.

d. Anti-Adhesion Component

The application of pressure is typically a key part of the hemostasis process. The application of pressure can have the undesired impact of having the hemostatic device stick to the puncture site 89. This can be problematic when coupled with the presence of blood on or around the puncture site 89, and such blood can form scabs while hemostasis is underway. Peeling away the hemostasis device upon the conclusion of hemostasis can thus often have the undesired impact of pulling the scab off of the puncture site 89. By reducing the friction between the apparatus 100 (and more specifically the bottom surface of the apparatus 100) with an anti-adhesion component 116, the problem of peeling the scab off is avoided because the apparatus 100 does not adhere to the scab.

FIG. 3*j* is a diagram illustrating an example of the apparatus 100 illustrated in FIG. 3*h* that includes an anti-adhesion component 116, such as a medical grade silicone coating. FIG. 3*k* is a diagram illustrating an example of the apparatus 100 illustrated in FIG. 3*i* that includes an anti-adhesion component 116, such as a medical grade silicone coating.

Whether the apparatus 100 is comprised of a stand-alone visual pulse indicator 110, or whether the visual pulse indicator 110 is part of a fully integrated or substantially integrated hemostasis apparatus 100, the bottom surface of the apparatus 100 (which will typically be either the visual pulse indicator 110 or its sheath 124), can benefit from the presence of a lubricating component or anti-adhesion component 116.

While a medical grade silicone coating or covering may be preferred to prevent the apparatus 100 from sticking to the scab, and thus not pulling it off when the apparatus 100 is removed, there are other materials that may also be applicable for this feature.

In different embodiments of the apparatus 100, the bottom surface of the apparatus can vary. In some instances, the bottom surface of the apparatus 100 may be part of a pressure component 108. In other embodiments, it may be part of the visual pulse indicator 110. However, it is the bottom surface of the apparatus 100 that comes into direct contact with the patient 90 on or relative to the puncture site 89, so the lubricating coating 116 must be on the bottom surface.

2. Timer Component

Hemostasis is temporary activity that typically involves hours to begin and complete. Before hemostasis begins, the provider 92 has an expected duration in mind. In some embodiments of the apparatus 100, it is helpful to include a timer component 112 to assist providers 92 by notifying them when pressure should either be adjusted or withdrawn altogether from the puncture site.

FIG. 4*a* is a diagram illustrating an example of a timing component 112 that can display elapsed time using a variety of different numerical metrics. An electronic stopwatch 126 is illustrated in FIG. 4*a*, although different types of prior art time monitoring technologies can be used in conjunction with the apparatus 100.

FIG. 4*b* is a diagram illustrating an example of a timing component 112 that is based on the release of ink within a strip 128. This approach graphically displays elapsed time not necessarily as a numerical metric, but instead in proportion to the total anticipated time.

It is envisioned that different timer components 112 can be made available for different embodiments of the apparatus 100. Those varying embodiments of timer components 112 will in different ways indicate how long pressure has been applied to the puncture site 89 during hemostasis. Subsequently, when the provider 92 attends to the patient 90, they can look at the timer component 112 and know how long pressure has been applied. A hemostasis band is usually worn for 2 hours. Some doctors prescribe decreasing the pressure in the balloon every 15 minutes. The timer component 112 could be valuable for monitoring the patient 112 while they are in recovery after the procedure. For embodiments of the apparatus that include a timer component 112, it is very convenient for the provider 92 to simply press a button or something similar to start the clock running.

Electronic timer components 126 can be configured to automatically interact with other electronic devices, send text message/e-mail alerts, etc.

3. Body Component

A body component 102 is the structure or mechanism used to keep the other components of the apparatus 100 together. In many embodiments, the body component 102 is a strap or band. For example, in the context of transradial catheterization, the body component 102 can be a strap or band that either fully or partially wraps around the arm of the patient 92.

The body component 102 can be made from a variety of different materials. For example, the body component 102 can be fully flexible, semi-rigid, or even fully rigid. In some instances it can be desirable for the body component 102 to be transparent to facilitate the functionality of a sensor component 110 or for some other purpose, while in other instances the body component 102 can be translucent or even opaque.

In some embodiments, the body component 102 is the same component as a fastening component 104. For example, an elastic band can serve as both the body component 102 and the fastening component 104.

Figure 5A:
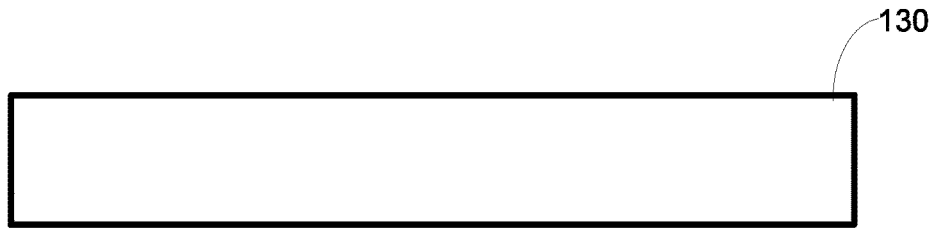
FIG. 5a is a diagram illustrating an example of a top-view of a band that can serve as a body component for the apparatus.

FIG. 5*a* illustrates an example of a body component 102 that is a band 130. The band 130 in FIG. 5*a* is flexible, and can be wrapped around an appendage of the patient 90. The band 130 in FIG. 5*a* does not form a continuous loop. To the contrary, it includes two ends which can then be connected through the use of a fastening component 104.

Figure 5B:
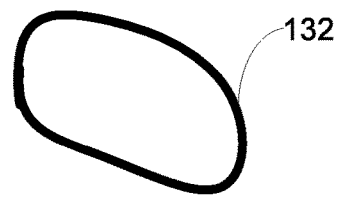
FIG. 5b is a diagram illustrating an example of a side-view of a band in the form of a continuous elastic loop, such as a rubber band or a nylon loop.

FIG. 5*b* illustrates an example of a body component 102 that is a continuous loop 132 that is at least substantially flexible. Thin flexible bands 132 such as the band 132 in FIG. 5*b* are particularly desirable in the context of a visual pulse indicator 110 that is separate from the hemostasis device that includes the pressure component 108 that applies pressure to the puncture site 89.

Figure 5C:
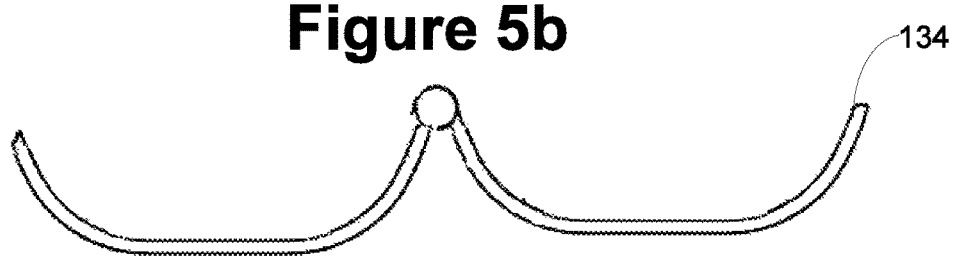
FIG. 5c is a diagram illustrating an example of a band with a hinge.

FIG. 5*c* illustrates an example of a body component 102 that is a band 134 that includes a hinge and is at least semi-rigid. Such a band 134 can be particularly desirable in the context of fully or substantially integrated hemostasis apparatus 100 that includes the key components in one convenient to use product.

4. Fastening Component

A fastening component 104 is potentially any mechanism or structure that can secure the apparatus 100 to the applicable location on the patient 90. Examples of fastening components 104 include buckles, snap-hooks, buttons, zippers, adjuster bars, slides, cord locks, zipper pulls, modular buckles, hook-and-loop fasteners, continuous elastic loops, continuous inflatable loops, fabric fastening tape comprised of a dense arrangement of tiny nylon hooks and an interlocking nylon pile (i.e. ®VELCRO), or any other example of a fastening technology or apparatus.

In some embodiments, the fastening component 104 is inherent in the nature of the body component 102. For example, no separate fastening component 104 is required if the body component 102 is an elastic loop 132 or an inflatable loop.

5. Padding Component

A padding component 106 is potentially any mechanism or structure that can make the apparatus 100 more comfortable for the patient 90. Each embodiment of the apparatus 100 will typically involve one or more padding components 106, such as adjustable pads, foam pads, or inflatable pads. In some instances, the padding component 106 is not separate and distinct from the body component 102. For example, in the context of an inflatable band serving as the body component 102, the body 102 itself can inherently possess the desired padding attributes.

Figure 6A:
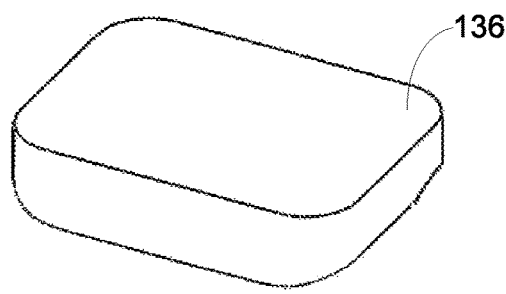
FIG. 6a is a diagram illustrating an example of a perspective view of a padding component in the form of a pad.

FIG. 6a is an illustration of a pad 136 as a padding component 106. Such a pad 136 can either be removably attached to the apparatus 100 or irremovably attached to the apparatus 100. Some pads 136 are designed to be movable along the body component 102 of the apparatus 100.

Figure 6B:
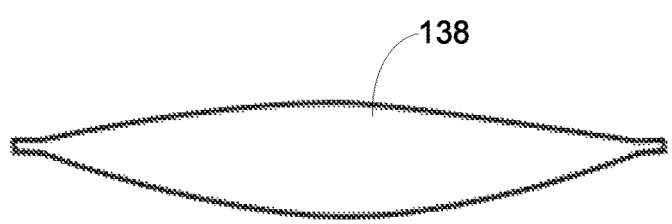
FIG. 6b is a diagram illustrating an example of a side view of a padding component in the form of a balloon.

FIG. 6b is an illustration of a balloon 138 as a padding component 106. In some instances, the pressure component 108, such as a balloon, can also serve as the padding component 106. However, it is often useful to have at least one padding component 106 to help diffuse the application of pressure along a greater surface area on the patient 90.

When balloons 138 as used as padding components 106, they can be inflated with air, liquid, or even mechanical mechanisms such as springs.

6. Pressure Component

A pressure component 108 is potentially any mechanism or structure that can apply pressure to the puncture site 89 of the patient 90.

a. Balloons

In many embodiments of the apparatus 100, the pressure component 108 is one or more balloons, such as a pneumatic balloon inflated with a gas such as air, a hydraulic balloon inflated with a liquid such as water or saline, an adjustable balloon of any type, a balloon shaped to guide the direction of force or pressure, or some other type of flexible material. In many embodiments of the apparatus 100, the pressure component 108 will be a substantially transparent balloon such as the balloon 140 illustrated on Figure ?a. Such a balloon 140 can be comprised of such as polyurethane or polyvinyl chloride (PVC).

Examples of non-balloon based pressure components 108 can utilize mechanical expansion rather than inflation of a balloon. A piston assembly 130 (see FIG. 6 as discussed below) is another example of a pressure component that is not a balloon. In many embodiments of the apparatus 100, the pressure component 108 is configured to gradually release pressure over a particular period of time. For example, in the context of transradial catheterization, it is desirable for pressure to automatically reduce over a period of time that is typically between 45-150 minutes.

In some embodiments, the pressure component 108 is not necessarily separate and distinct from the body component 102. For example, in the context of an inflatable band serving as the body component 102, the body 102 can inherently possess the desired attributes of the pressure component 108.

b. Sensor Enhancement Component

Visual pulse indicators 110 utilize thin flexible film to translate pulse motions at the puncture site 89 into visible indicia displayed by the visual pulse indicator 110. In some instances and in some embodiments, it may be desirable to enhance the sensitivity of the visual pulse indicator 110 through the use of a sensor enhancement component 114, such as a "middle member" or "air pocket" as disclosed in FIG. 7b. By aligning the sensor enhancement component 114 in the bottom center of the balloon 140, the pulsing motions of the artery and blood flow will be amplified onto to the visual pulse indicator 110.

c. Slide Openings

Figure 7C:
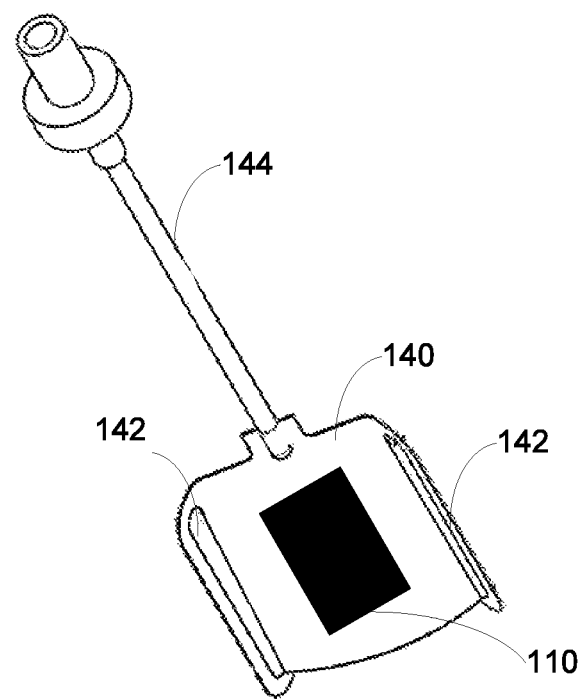
FIG. 7c is a diagram illustrating an example of a top-view of a balloon with a visual pulse indicator attached to the balloon.
Figure 7D:
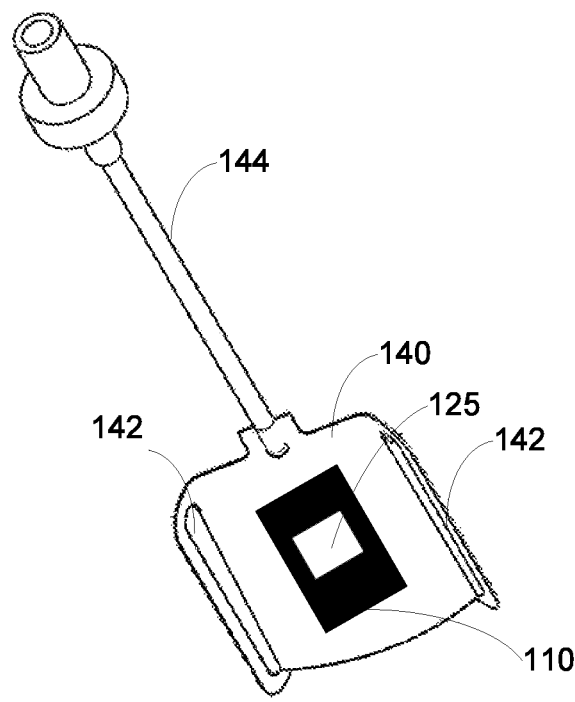
FIG. 7d is a diagram illustrating an example of a top-view of a balloon with a visual pulse indicator attached to the balloon and where there is a window in the visual pulse indicator.

As illustrated in FIG. 7c, the balloon 140 can incorporate openings 142 or gaps 142 that allow the balloon 140 to slide along the body component 102 of the apparatus 100. Typically the slide openings 142 are comprised of the same material as the balloon 140 itself.

As illustrated in FIG. 7c, an inlet 144 into the balloon is the means by which the balloon 140 is inflated. The inlet 144 may include a valve or cap for maintaining and adjusting inflated pressure.

e. Visual Pulse Indicator

As discussed above, the balloon 140 can be an excellent location for the visual pulse indicator 110 because of the inherent flexibility of the balloon 140. FIG. 7c illustrates an example of how the visual pulse indicator 110 can be enclosed within the balloon 140. This can be done with or without a sheath 124. In FIGS. 8a-8f a visual pulse indicator 110 can be added (with or without a sheath 124).

f. Piston Assembly

Figure 7E:
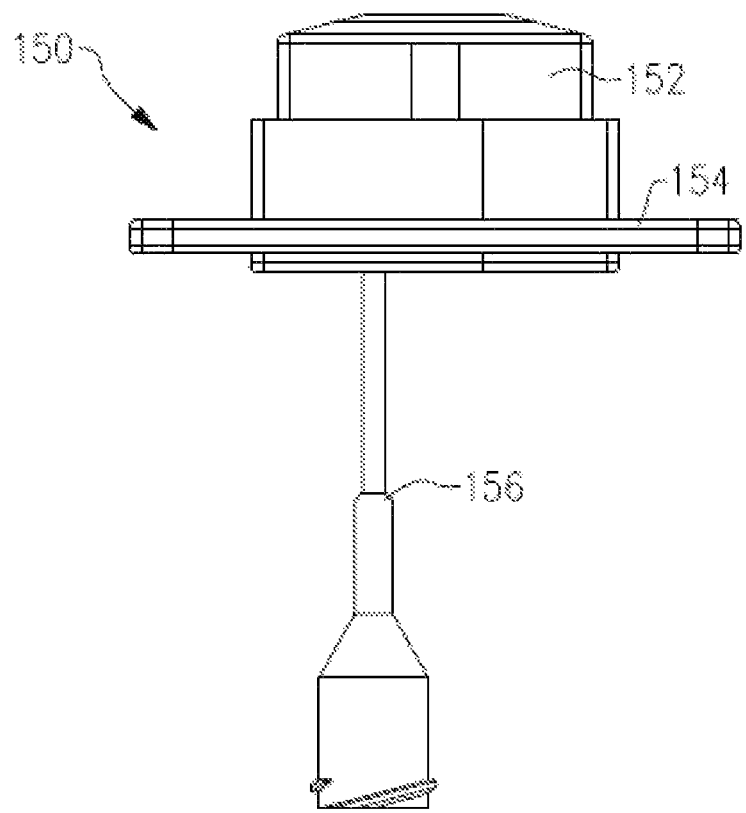
FIG. 7e is a diagram illustrating an example of a side-view of a pressure component in the form of a piston.
Figure 8A:
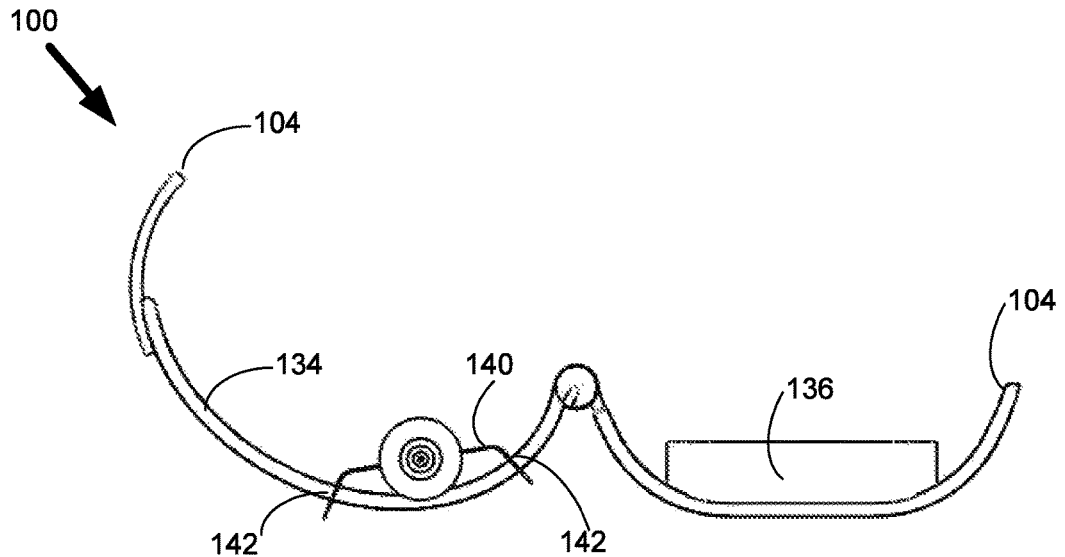
FIG. 8a is a diagram illustrating an example of a bottom-view of an open hemostasis band.
Figure 8B:
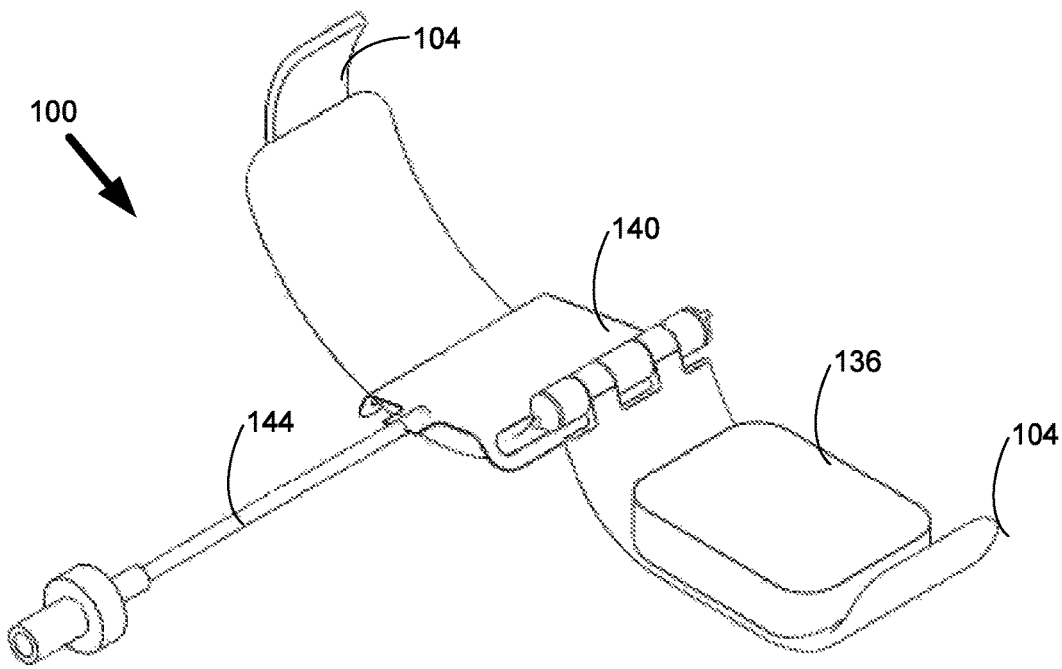
FIG. 8b is a diagram illustrating an example of a perspective-view of an open hemostasis band.
Figure 8C:
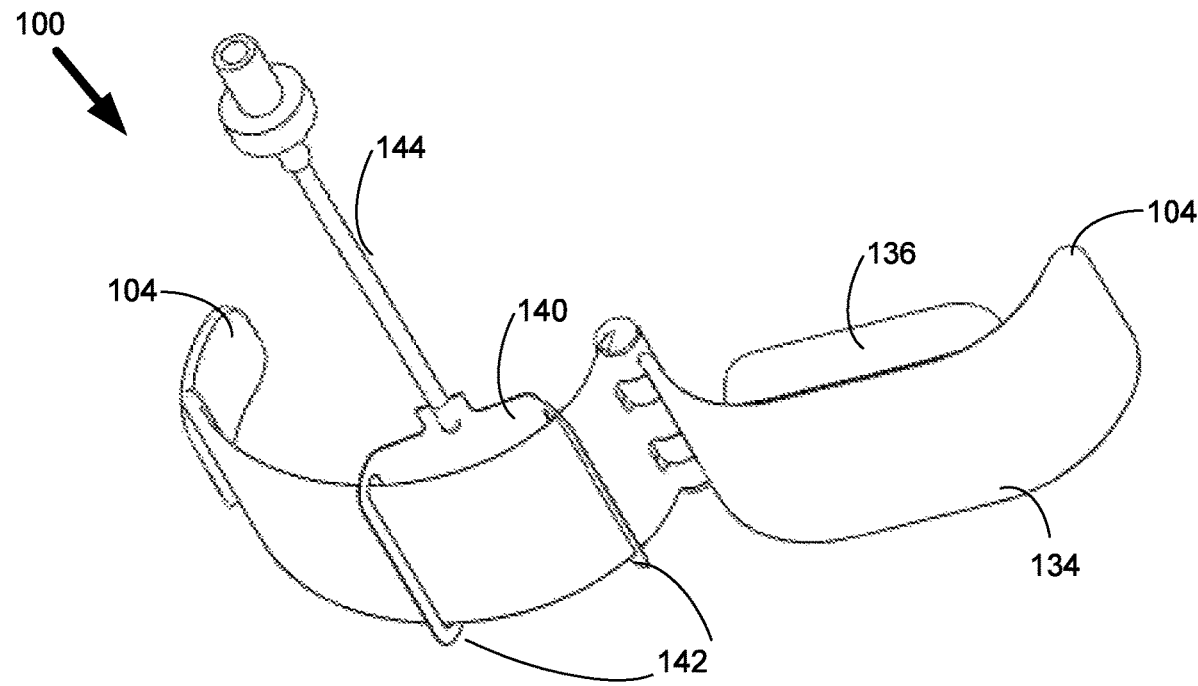
FIG. 8c is a diagram illustrating an example of a perspective-view of an open hemostasis band.
Figure 8D:
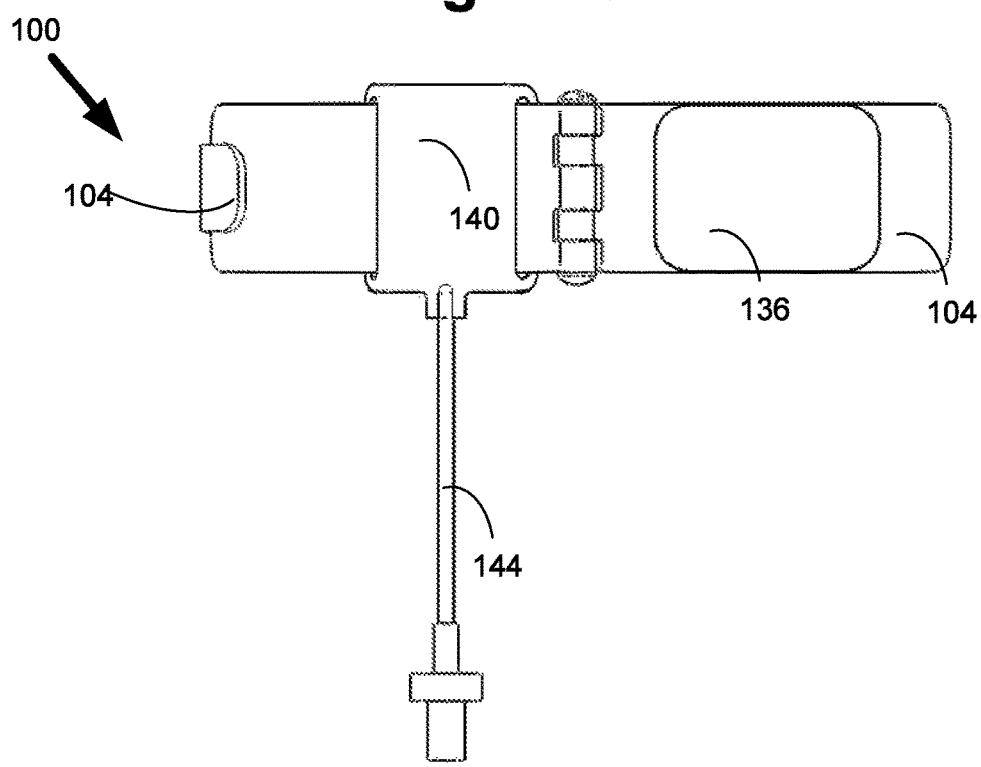
FIG. 8d is a diagram illustrating an example of a side-view of an open hemostasis band.
Figure 8E:
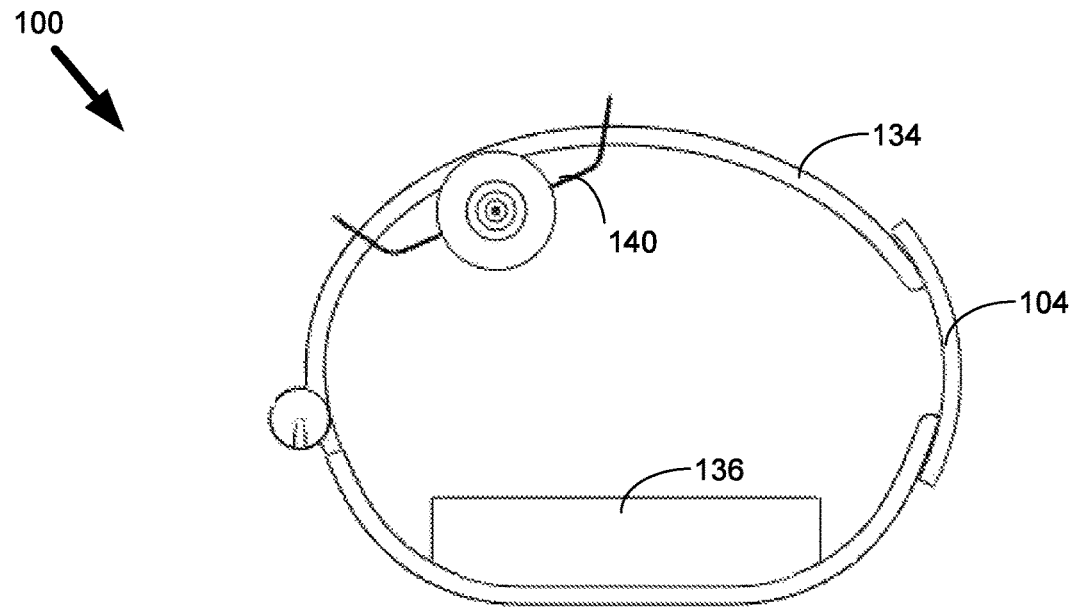
FIG. 8e is a diagram illustrating an example of a hemostasis band illustrated in FIG. 8a, except in a closed position.
Figure 8F:
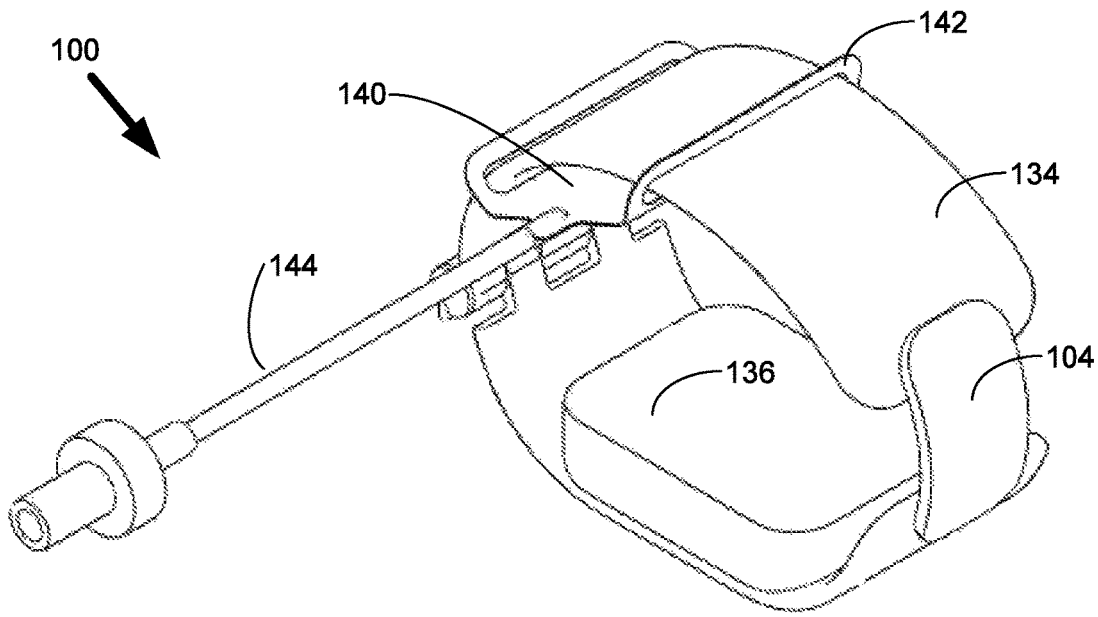
FIG. 8f is a diagram illustrating an example of a perspective view of a closed hemostasis band.

FIG. 7e illustrates an example of a piston assembly 150 that can constitute an alternative to a balloon 140 as a pressure component 108. As discussed above, a piston assembly 150 can serve as a pressure component 108 for the apparatus 100. FIG. 6 illustrates an example of a piston assembly 150 in the form of a piston-and cylinder design.

As illustrated in FIG. 7e, the piston assembly 150 can include a soft silicone floating piston 152, an oval cylinder 154, and an inflation tube 156.

The oval cylinder 154 can be connected to the body component 102 of the apparatus 110, or it may be an integral part of the body component 102. The piston 152 portion would be actuated to apply the necessary force or pressure over the incision area. The piston 152 may be actuated pneumatically, but other means of actuation are possible and envisioned. The piston 152 may be actuated mechanically, for example with a thread design like a power screw. This design of a pressure component 108 could be adjusted as necessary while the apparatus 100 is being put on the patient 90 or while the apparatus 100 is being used during recovery. The piston 152 would be made from any of a variety of applicable materials, for example a soft durometer silicone. The size and shape of the piston component 152 can be any of a variety of sizes or shapes if they provide an advantage or convenience to the patient 90, provider 92 or apparatus 100. The size or shape may provide advantage of safety, comfort, design or manufacturing.

IV. Integrated Embodiments

It will often be desired to implement the apparatus 100 as a substantially integrated device that includes most if not all of the components that can be integrated into the apparatus 100. FIGS. 8a-8f illustrate different views of a substantially integrated apparatus 100. For the sake of avoiding drawing clutter, the visual pulse indicator 110 and its sheath 124 are omitted from each of the drawings. Optional features such as timer components 112, anti-adhesion components 116, and sensor enhancement components 114 could also be added to the illustrated apparatus 100 as desired.

V. Non-Integrated Embodiments

Non-integrated embodiments can involve the same components as discussed above and as illustrated in FIGS. 8a-8f. The only difference between integrated embodiments and non-integrated embodiments is whether all of the different components are in some way attached to the same device.

For example, a visual pulse indicator 110 (with or without a sheath 124) could be placed on the puncture site 89 without any connection to any device or component. Whatever pressure component 108 is used to apply pressure to the puncture site 89 would keep the visual pulse indicator 110 in place. Alternatively, a small thin elastic strap 132 could be used in conjunction with the visual pulse indicator 110, with another hemostasis device being responsible for the application of pressure and other functions.

The invention claimed is:

1. An apparatus for use over a puncture site for a patient during hemostasis comprising:
a visual pulse indicator that is configured to be positioned on the patient near the puncture site, wherein said visual pulse indicator provides for displaying a plurality of indications that relate to a plurality of blood flow attributes, wherein said visual pulse indicator is a reflective foil that provides for moving up and down along with a pulse of said patient, said reflective foil having a first side and a second side, said first side configured to be placed facing the patient's skin near the puncture site; and
a pressure component configured to apply pressure to said puncture site, wherein said pressure component is a substantially transparent balloon, and wherein said pressure component is attached to one of said first side and said second side of said reflective foil;
said plurality of indications including a first indication and a second indication;
said plurality of blood flow attributes including a constricted blood flow and a non-constricted blood flow;
wherein said first indication is displayed in conjunction with said non-constricted blood flow;
wherein the reflective foil visually shows the moving up and down along with the pulse of the patient.

2. The apparatus of claim 1, wherein the hemostasis is performed as part of a transradial catheterization on the patient.

3. The apparatus of claim 1, wherein said reflective foil is comprised of a polyester.

4. The apparatus of claim 1, said apparatus further comprising a body component, wherein said body component is a band, wherein said substantially transparent balloon is movable along said band, and wherein said substantially transparent balloon provides for being removed from said band.

5. The apparatus of claim 1, said apparatus further comprising a bottom surface coated with an anti-adhesion component.

6. The apparatus of claim 5, wherein the anti-adhesion component is a silicone coating.

7. The apparatus of claim 1, said apparatus further comprising a timing component that provides for conveying a duration after which pressure on the puncture site is to be adjusted.

8. The apparatus of claim 1, wherein said visual pulse indicator is integrated with said balloon.

9. The apparatus of claim 8, wherein a surface of said balloon that is attached to said reflective foil is thicker at a center portion of said balloon than at a side portion of said balloon.

10. The apparatus of claim 8, said apparatus further comprising a centering member positioned on a surface of said balloon that is attached to said reflective foil to enhance the sensitivity of said visual pulse indicator.

11. The apparatus of claim 8, said apparatus further comprising a band, wherein said balloon provides for being temporarily secured to said band, and wherein said balloon includes a plurality of slide openings that provide for the movement of said balloon along said band.

12. The apparatus of claim 1, wherein the visual pulse indicator provides a visual indication of a physical pulsing motion of an artery near the puncture site.

13. The apparatus of claim 1, wherein the visual pulse indicator is arranged at or downstream of the puncture site.

14. The apparatus of claim 1, wherein the visual pulse indicator has a moire line pattern.

15. An apparatus for use over a puncture site for a patient during hemostasis, comprising:
a visual pulse indicator that is configured to display a blood flow attribute relating to the puncture site;
a body component, wherein said visual pulse indicator is attached to said body component, and the body component is configured to position the visual pulse indicator on the patient downstream from said puncture site; and
a balloon, wherein said balloon is attached to said body component and said visual pulse indicator, wherein the inflation of said balloon provides for increasing the pressure at the puncture site, wherein said visual pulse indicator is integrated with said balloon, and wherein a first side of a reflective foil is configured to be placed in direct contact with the patient's skin.

\* \* \* \* \*